(12) United States Patent
Schmid et al.

(10) Patent No.: US 9,833,385 B2
(45) Date of Patent: Dec. 5, 2017

(54) DEVICE FOR DETECTING THE REMOVAL OF DRUGS

(71) Applicants: SEIBERSDORF LABOR GMBH, Seibersdorf (AT); AIT AUSTRIAN INSTITUTE OF TECHNOLOGY GMBH, Vienna (AT)

(72) Inventors: Gernot Schmid, Bromberg (AT); Manfred Bammer, Vienna (AT)

(73) Assignees: Seibersdorf Labor GmbH, Seibersdorf (AT); AIT Austrian Institute of Technology GmbH, Vienna (AT)

( * ) Notice: Subject to any disclaimer, the term of this patent is extended or adjusted under 35 U.S.C. 154(b) by 0 days.

(21) Appl. No.: 15/118,187

(22) PCT Filed: Feb. 2, 2015

(86) PCT No.: PCT/AT2015/050033
§ 371 (c)(1),
(2) Date: Aug. 11, 2016

(87) PCT Pub. No.: WO2015/120497
PCT Pub. Date: Aug. 20, 2015

(65) Prior Publication Data
US 2017/0172851 A1    Jun. 22, 2017

(30) Foreign Application Priority Data

Feb. 11, 2014    (AT) .............................. A 50103/2014
Mar. 10, 2014    (AT) .............................. A 50173/2014

(51) Int. Cl.
*G08B 21/00*     (2006.01)
*A61J 7/02*     (2006.01)
(Continued)

(52) U.S. Cl.
CPC ................. *A61J 7/02* (2013.01); *A61J 1/035* (2013.01); *A61J 7/0481* (2013.01);

(58) Field of Classification Search
CPC .. A61J 7/02; A61J 7/0481; A61J 1/035; G06F 19/3462; G06K 19/07749; G06K 19/07798; B65D 83/0463; B65D 75/36
(Continued)

(56) References Cited

U.S. PATENT DOCUMENTS 4,616,316 A * 10/1986 Hanpeter .............. A61J 7/0481
                                                                  206/531
4,617,557 A * 10/1986 Gordon ................. A61J 7/0472
                                                 206/531
(Continued)

FOREIGN PATENT DOCUMENTS

DE       102012005443 A1    9/2013
WO         8909042 A1    10/1989

*Primary Examiner* — John A Tweel, Jr.
(74) *Attorney, Agent, or Firm* — Laurence A. Greenberg; Werner H. Stemer; Ralph E. Locher

(57) ABSTRACT

A device detects the removal of drugs from a drug blister pack. The device has a base for receiving the drug blister pack and a base surface which is configured for contact with the electrically conducting foil that doses the pockets of the blister pack. In the region of the pockets, the base has holes that are configured for the passage of the drugs present in the pockets, every hole being arranged in the region of one of the pockets. A coil is arranged in the region of each of the holes and extends around the respective hole, in particular exclusively the respective hole. A detector unit is provided which produces an electrical field and/or magnetic field in the region of one or more holes by one of the coils and analyzes the voltage or the current on at least one of the coils extending around the hole.

19 Claims, 13 Drawing Sheets

(51) Int. Cl.
*A61J 1/03* (2006.01)
*H04B 5/00* (2006.01)
*G07C 1/02* (2006.01)
*A61J 7/04* (2006.01)
*G06F 19/00* (2011.01)
*G06K 19/077* (2006.01)

(58) Field of Classification Search
USPC .................................................. 340/661
See application file for complete search history.

(56) References Cited

U.S. PATENT DOCUMENTS

| | | |
|---|---|---|
| 4,660,991 A | 4/1987 | Simon |
| 5,072,430 A | 12/1991 | Eckernaes et al. |
| 5,836,474 A * | 11/1998 | Wessberg .............. A61J 7/0481 221/2 |
| 6,973,371 B1 * | 12/2005 | Benouali ................ A61J 1/035 221/15 |
| 8,091,790 B2 * | 1/2012 | Mickle ............ G06K 19/07749 235/435 |
| 8,120,492 B2 * | 2/2012 | Scharfeld ......... G06K 19/07749 340/572.1 |
| 2003/0111477 A1 * | 6/2003 | Niemiec ................ A61J 7/0481 221/2 |
| 2005/0241983 A1 | 11/2005 | Snyder et al. |
| 2006/0144747 A1 * | 7/2006 | Le ........................ A61J 7/0481 206/531 |
| 2009/0283439 A1 * | 11/2009 | Barndt ................ B65D 83/0463 206/531 |

\* cited by examiner

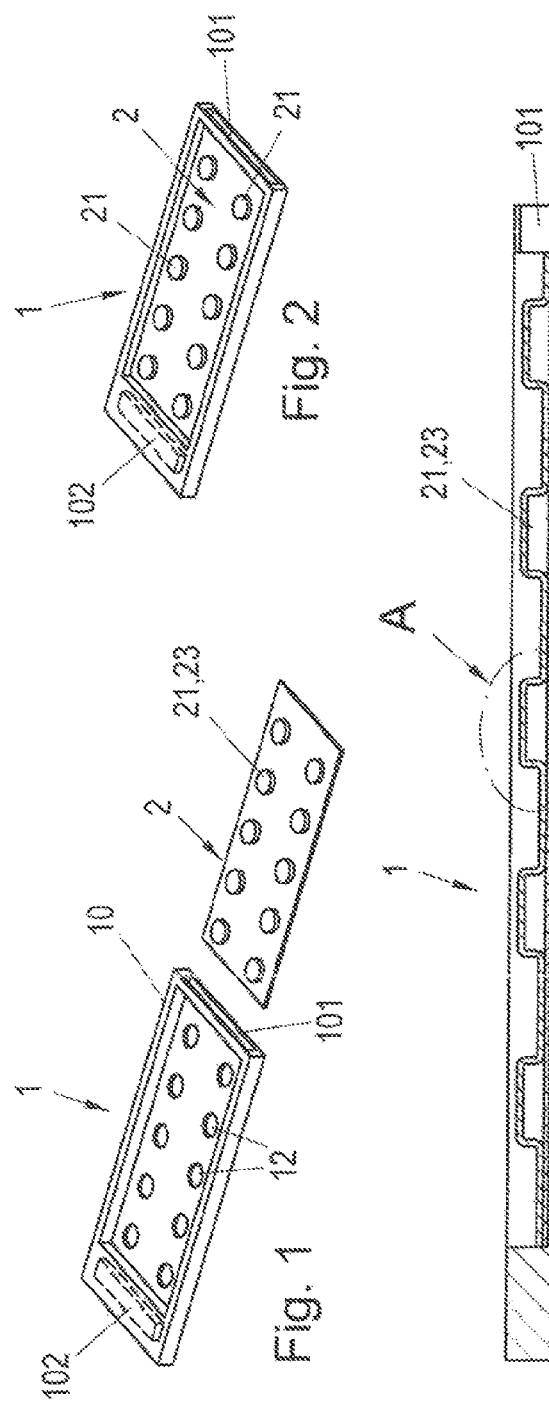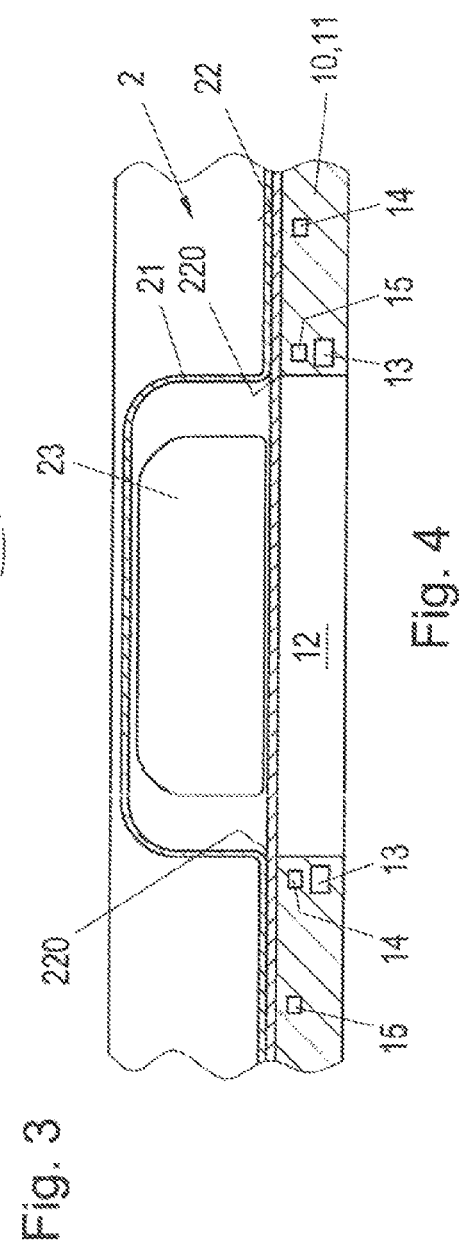

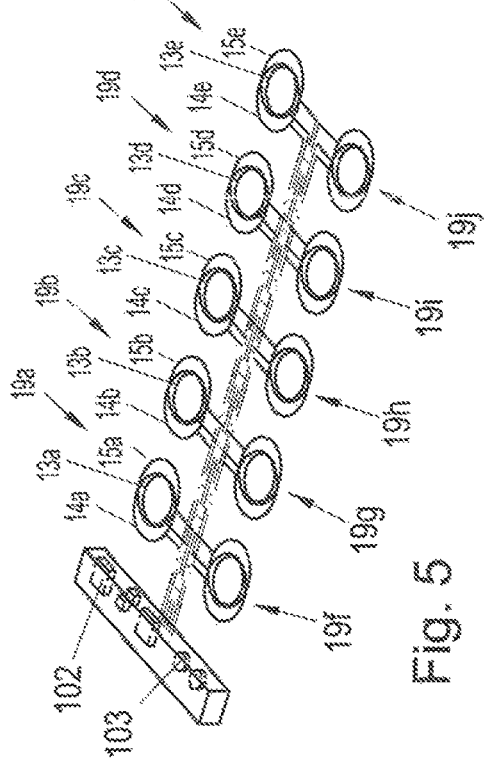

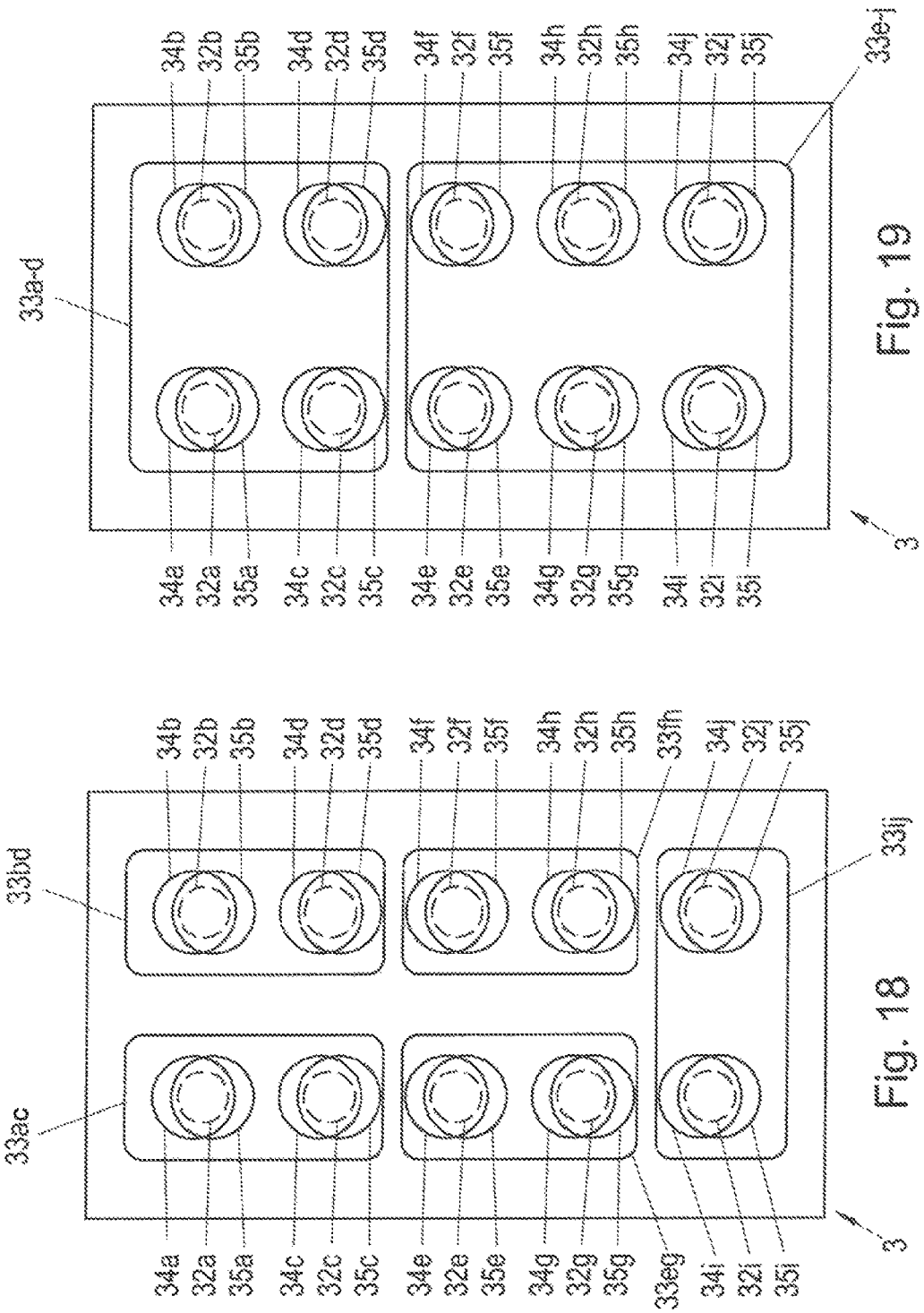

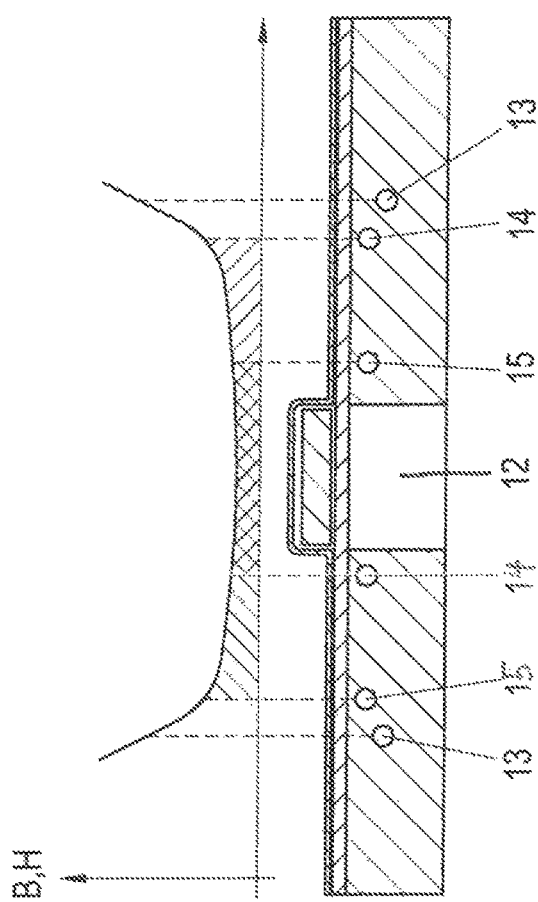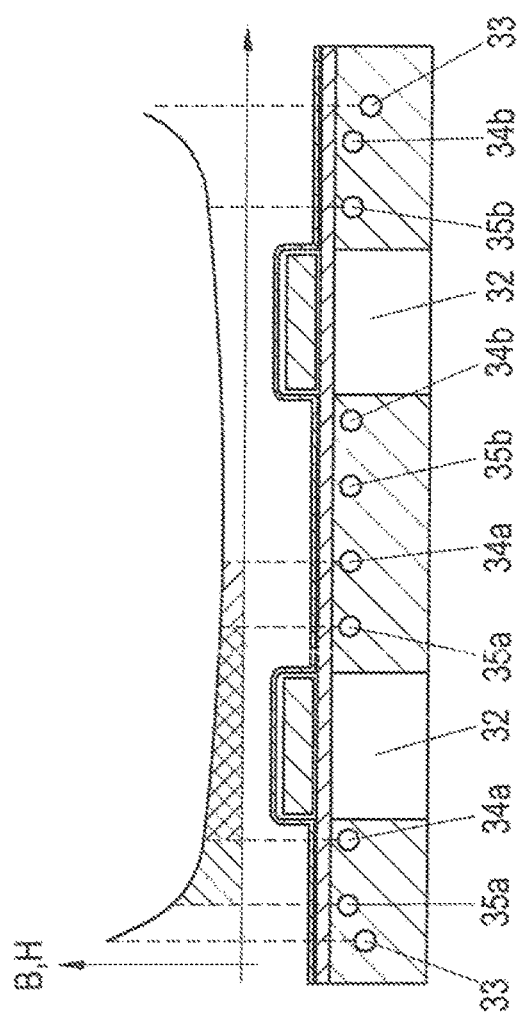

DEVICE FOR DETECTING THE REMOVAL OF DRUGS

BACKGROUND OF THE INVENTION

Field of the Invention

The invention relates to an apparatus for detecting the removal of medicaments from a drug blister pack.

The incorrect use of drugs constitutes a great problem in practice. In the case of a correct diagnosis and an ideal therapy plan, the success of the therapy can be drastically reduced if the patient does not use the drug correctly. In the case of some medicaments, e.g. anticoagulants, incorrect use can even have life-threatening consequences. The sources of error are multifaceted in practice: patients do not take medicaments or take the wrong medicaments; they take the correct medicaments in doses which are too small or too large. The World Health Organization WHO estimates that every second patient does not follow the instructions on the information leaflet or instructions by the medical practitioner. Experts assume that every fourth hospitalization and many deaths in Germany—more than 40,000 per annum with "cardiovascular" indications alone—can be traced back to incorrect use of medicaments. The reliable detection of correct and regular medicament uptake by the patients is therefore desirable, at least for certain classes of medicaments, firstly for health reasons and secondly for insurance purposes.

The currently existing solution approaches for detecting the tablet removal from press-through blister packs only have very restricted suitability for the mass market and have not yet prevailed because they are too complicated in terms of handling and manufacturing. These methods are based on the idea of destroying electrical conductor paths, antenna structures, components of resistor networks, etc. by pressing out the tablets, which is easily detectable by electronics connected to these structures. To this end, these structures, such as conductor paths, antennas, resistor networks, etc., must either be integrated directly into the sealing foil of the blister pack or subsequently applied onto the sealing foil, for example in the form of an adhesive foil, which contains the aforementioned structures with precise fit for each blister pack.

Therefore, relatively small clinical studies are currently based on the approach with foils which contain the aforementioned structures and are retrospectively adhered with precise fit onto the lower side of standard blister packs. As a result of the targeted provision of predetermined breaking points in the foil, the latter is pressed through or ripped open together with the blister pack sealing foil within the process of removing the tablet, and the structure element assigned to the respective blister pack pocket or tablet, e.g. a conductor path, antenna, etc., is destroyed or made inoperable. By way of electronics assigned to the structure elements, e.g. which are electrically connected to the foil by a contact strip, it is possible to record the time of the tablet removal and what tablet was removed.

The main problem of these solution approaches is the fact that the detection of the tablet removal is based on the destruction of the foil with the structure elements which was adhered onto the blister pack with precise fit. Therefore, a new foil with structure elements is required for each blister pack, leading to a linear increase of the costs with the number of required medicament blister packs. The alternative approach of already integrating the structure elements into the blister pack sealing foil is considered by the medicament producers as requiring too much outlay from a production point of view, being too complicated from a regulatory point of view and being unacceptable in view of the costs for the medicament packaging.

A solution with a reusable detection element for monitoring the tablet removable would therefore not only be paid back very quickly in large studies or within the scope of mass use during routine, but would also render obsolete the production of highly specialized blister packs.

BRIEF SUMMARY OF THE INVENTION

It is therefore an object of the invention to simplify the detection of the tablet removal and to provide an apparatus which enables the detection even if the tablet producer has not provided such a possibility.

The invention solves this problem in the case of an apparatus of the type set forth at the outset by way of the features of the main patent claim.

An apparatus according to the invention for detecting the removal of medicaments from a drug blister pack comprises a main body for accommodating the drug blister pack with a base area, which is embodied to rest against the electrically conductive, in particular metallic foil which seals off the pockets of the blister pack, wherein the main body has holes in the region of the pockets of the blister pack, said holes being embodied for the passage of the medicaments situated in the pockets of the blister pack. Furthermore, provision is made for each hole to be arranged in the region of one of the pockets in each case,
  at least one coil to be arranged in the region of each hole, which coil surrounds the respective hole, in particular only surrounds the respective hole, and provision to be made of a detector unit, which generates an electric and/or magnetic field in the region of one or more holes by means of one of the coils and evaluates the voltage across or the current applied to at least one of the coils surrounding the hole, in particular only this hole.

By means of such an apparatus, it is easily possible to detect the removal of medicaments from the blister pack without the blister pack needing to have special features to this end.

In a preferred apparatus for detecting the removal of medicaments from a drug blister pack, comprising a main body for accommodating the drug blister pack with a base area, which is embodied to rest against the electrically conductive, in particular metallic foil which seals off the pockets of the blister pack, provision is advantageously made for the main body to have holes in the region of the pockets of the blister pack, said holes being embodied for the passage of the medicaments situated in the pockets of the blister pack, wherein each hole is arranged in the region of one of the pockets in each case,
  wherein one transmission coil and at least two reception coils are arranged in the region of the holes in each case, said coils surrounding the respective hole, and
  wherein the reception coils are assigned to one another in respect of the transmission coil and arranged in such a way that, in the case where the foil resting on the main body in the region of the respective hole is undamaged, in particular free from rips, the difference of the voltages induced in the reception coils as a result of an electric current in the transmission coil lies below a predetermined threshold.

A simple detection of the opening of a pocket of a drug blister pack, which can easily be carried out, is made possible as a result of this measure.

A possible development of the invention enabling a precise detection provides for a transmission coil to be present, said transmission coil surrounding at least one of the holes, in particular all holes, and for at least one reception coil to be arranged in the region of the holes in each case, said reception coil surrounding the respective hole, in particular only this hole.

A possible development of the invention enabling a detection of a rip with simple means provides for at least two reception coils to be arranged in the region of the holes in each case, said reception coils surrounding the respective hole, in particular only this hole.

A further improvement in the precision of the detection can be achieved if a separate transmission coil is present in each case for each of the holes.

The detection of a rip can be simplified further if the reception coils are assigned to one another in respect of the transmission coil and arranged in such a way that, in the case where the foil resting on the main body in the region of the respective hole is undamaged, in particular free from rips, the difference of the voltages induced in the reception coils as a result of an electric current in the transmission coil lies below a predetermined threshold.

An advantageous implementation of an automated detection can be obtained by virtue of a detector unit which activates the transmission coil and measures the voltages across the reception coils and which establishes the difference between the voltages across the reception coils and, in the case where the difference of the two voltages exceeds a predetermined threshold, and in this case emits a message which indicates the presence of a rip in the metal foil sealing the respective pocket.

A development of the invention with a simplified design provides for the detector unit to comprise the following:
  a control unit which activates the transmission coil,
  a measuring unit which measures the voltages across the reception coil or across the reception coils,
  a reference value storage for storing all measured voltages at an initial time, in particular after a new, undamaged drug blister pack was placed into the apparatus, and
  a comparison unit for determining the removal of medicaments from the drug blister pack, said comparison unit establishing the difference in each case between the voltage stored by the reference value storage and the voltage currently established by the measuring unit and the comparison unit outputting a message in the case where this difference exceeds a predetermined threshold which indicates the presence of a rip in the metal foil sealing the respective pocket in the region of the reception coils.

A simple detection of rips can be achieved by virtue of the detector unit comprising the following:
  a control unit which activates the transmission coil,
  a measuring unit which measures voltages across the reception coils and establishes the voltage difference of these measured voltages,
  a reference value storage for storing all established voltage differences at an initial time, in particular after a new, undamaged drug blister pack was placed into the apparatus, and
  a comparison unit for determining the removal of medicaments from the blister pack, said comparison unit establishing the difference in each case between the voltage difference stored by the reference value storage and the voltage difference currently established by the measuring unit and the comparison unit outputting a message in the case where this difference exceeds a predetermined threshold which indicates the presence of a rip in the metal foil sealing the respective pocket in the region of the reception coils.

A particularly simple embodiment of the invention provides for
  in each case one, in particular exactly one, separate coil surrounding the hole to be provided for each hole,
  the detector unit to apply an electric voltage across the coil and measure the electric current flowing through the coil and, from this, establish the impedance of the coil and/or, if need be, the resistance and reactance of the coil, and
  the detector unit to identify the exceeding of a predetermined impedance threshold and/or predetermined thresholds for the resistance and reactance of the coil and in this case output a message which indicates the presence of a rip in the metal foil sealing the respective pocket in the region of the coil.

In order to have the removal information available for further processing, provision can be made of a recording unit, which activates the detector unit at predetermined intervals and establishes the presence of rips in the foils sealing off the pockets of the blister pack and stores information in this respect in a storage and keeps it available for further queries.

A simple data interchange is ensured by virtue of
  a short-range radio module, comprising an antenna and a communication controller, being connected to the detector unit and
  a storage, if a rip in the foil is identified, storing a message in this respect, in particular with the additional provision of a timestamp, wherein the detector unit is able to transfer information stored in the storage to an external data communications device.

An advantageous data interchange by way of RFID/NFC becomes possible if the short-range radio module is an RFID or NFC transponder, comprising a transponder antenna and a communication controller.

Here, for the simple and interference-free transfer to an external data communications device, provision is advantageously made for the transponder antenna to extend at least in part along the outer boundary of the main body of the apparatus.

Alternatively, the short-range radio module can also operate on the basis of a Bluetooth standard, wherein it has an antenna and a communication controller.

An advantageous evaluation of a pocket of a drug blister pack provides that provision is made for an excitation unit, which is connected to the transmission coil, and provision is made for two measuring units, which are connected to the reception coils, and the detector unit has a control unit, which actuates the excitation unit to excite the transmission coils and actuates the measuring units to measure the induction voltages across the reception coils, establishes the difference of the established induction voltages and outputs a signal in the case where the magnitude of the difference exceeds a predetermined threshold.

A simple evaluation of a multiplicity of pockets of a drug blister pack provides for a multiplexer for selecting a group, in each case comprising transmission and reception coils assigned to one another, to be connected to the detector unit, wherein the multiplexer has a common input for actuating the respective transmission antenna and two common outputs for obtaining the induction voltages obtained from the reception coils, wherein the common input is connected to the excitation unit and the common outputs are each connected to one of the measuring units, wherein the multiplexer has groups, each comprising two multiplex inputs and one multiplex output, which are addressable together and are each connected to the transmission and reception antennas, which are assigned to one another and arranged in the region of the same hole.

A particularly exact detection in the case of a simple design is achieved by virtue of the reception coils being arranged in symmetric fashion in respect of the holes and in respect of the transmission coil.

A simple design provides for the detector unit and the short-range radio module to be housed in a separate housing and the detector unit to be electrically connected by way of electric contacts, which are separable in a non-destructive manner, to the transmission antennas and reception antennas arranged at or in the main body.

What is furthermore particularly advantageous is an arrangement comprising an apparatus according to the invention and a drug blister pack with a number of pockets which are adjacent to the holes and in each case contain a medicament, and a foil sealing off the pockets, said foil being adjacent to the base area, wherein a group comprising a transmission coil and at least two reception coils in each case lies opposite each hole.

A plurality of preferred embodiments of the invention are illustrated in more detail on the basis of the following figures of the drawing.

BRIEF DESCRIPTION OF THE SEVERAL VIEWS OF THE DRAWING

FIG. 1 shows a first embodiment of an apparatus for detecting the removal of medicaments and a drug blister pack.

FIG. 2 shows the apparatus depicted in FIG. 1, with the drug blister pack inserted into the apparatus.

FIG. 3 shows the combination depicted in FIG. 2, comprising the apparatus and the drug blister pack, in a cross section.

FIG. 4 shows a detail from FIG. 3.

FIG. 5 shows a circuit and an arrangement of transmission and reception coils.

FIG. 6 shows the transmission and reception coils depicted in FIG. 5 embedded in the apparatus for detecting the removal of medicaments.

FIG. 7 shows the field conditions in the region of a pocket of the medicament container in a sectional illustration.

FIG. 8 shows a section through the blister pack and the curve of the component of the field strength or flux density of the magnetic field generated by the transmission coil, or the component thereof normal to the foil of the blister pack.

FIGS. 16 to 19 show apparatuses in accordance with a second embodiment of the invention, comprising one or more common transmission coils and in each case two reception coils per hole.

FIG. 20 shows the field conditions in the region of a pocket of the medicament container in a sectional illustration in an apparatus as depicted in FIGS. 16 to 19.

DESCRIPTION OF THE INVENTION

Figure 9:
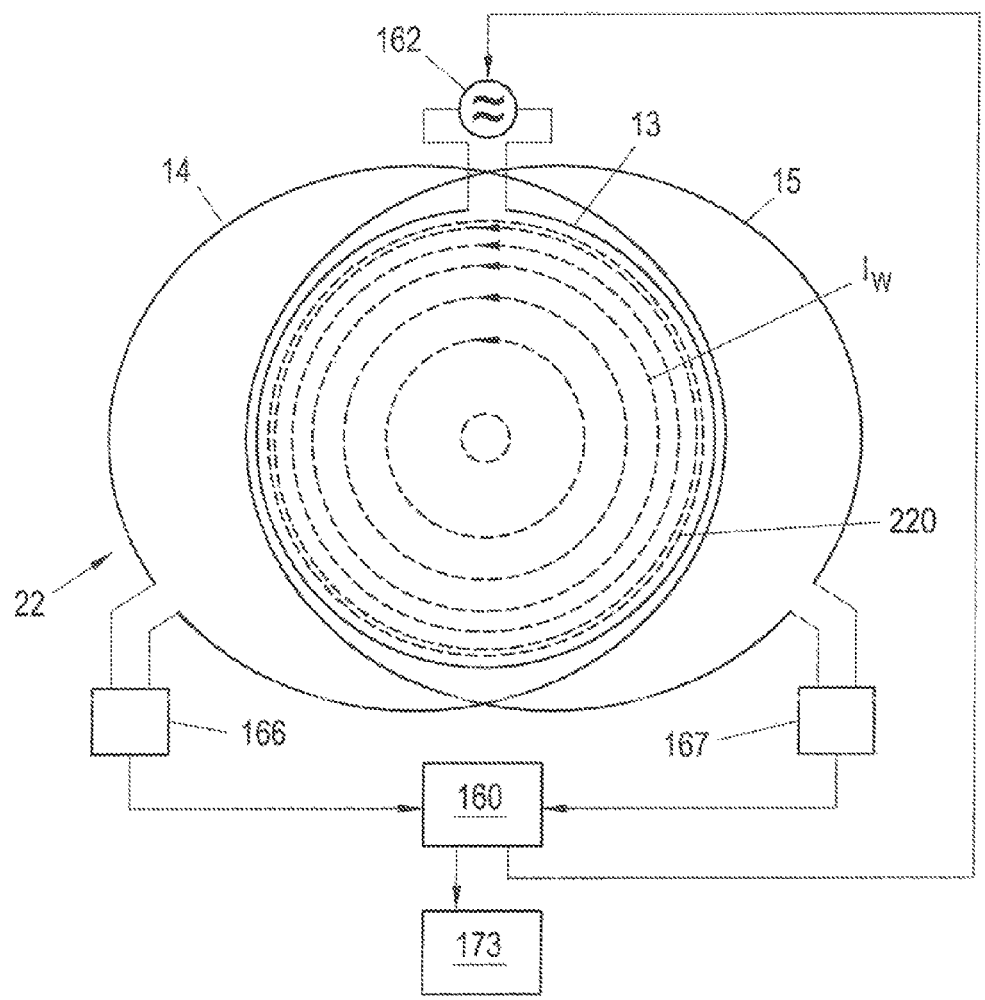
FIG. 9 shows, in detail, the field conditions in the region of an unopened and undamaged drug pocket, and the actuation and the readout of the transmission and reception coils.

FIG. 1 depicts a first embodiment of an apparatus according to the invention for detecting the removal of medicaments 23 from a drug blister pack 2. The apparatus 1 comprises a main body 10 with an opening 101 for inserting the drug blister pack 2 into the main body 10. At the position at which the pockets 21 of the blister pack 2 containing medicaments 23 are situated, the main body 10 of the apparatus 1 has a hole 12 in each case. Therefore, the pockets 21 lie directly opposite to the holes 12 such that the medicaments 23 situated in the pockets 21 of the blister pack 2 can be removed from the pockets 21, out of the blister pack 2 and out of the apparatus 1 through the holes 12.

FIG. 2 shows the drug blister pack 2 pushed through the opening 101.

FIG. 3 depicts the combination of the apparatus for detecting the removal of medicaments 23 and the drug blister pack 2 in a side view. FIG. 4 shows detail A from FIG. 3. Here, the region around the remaining pockets is embodied like in the region around the pocket 21 depicted in detail A. The pocket 21 constitutes a bulge in the drug blister pack 2, in which the medicament 23 to be removed, which is embodied as a tablet 23 in the present case, is situated. The pocket 21 is covered by an electrically conductive foil 22 in the planar continuation of the body of the drug blister pack 2, said foil sealing the pocket 21, wherein the foil 22 contains at least one planar continuous, electrically conductive layer or consists thereof. Three coils, namely a transmission coil 13 and two reception coils 14, 15, are situated in the region of the pocket.

FIG. 5 depicts the electronic and electrical components of the apparatus. Overall, FIG. 5 shows ten groups 19a . . . 19j of transmission coils 13a . . . 13j and reception coils 14a . . . 14j, 15a . . . 15j assigned to one another. Each group 19a . . . 19j determines the opening of in each case one of the pockets 21 of the blister pack 2. FIG. 5 also depicts an electronic circuit 102, which realizes a control unit 160 or detector unit 16 (FIG. 12), and a voltage supply 103.

FIG. 6 shows the apparatus with housing thereof, in which the transmission and reception coils 13, 14, 15, depicted in FIG. 5, are arranged, in particular cast or printed. Furthermore, FIG. 6 depicts an additional transmission antenna 191, by means of which the data established in the context of the medicament removal can be transferred to an external data communications device. In the present exemplary embodiment, the transmission antenna 191 extends along the outer boundary of the main body 10 of the apparatus 1.

In this configuration and in the case of an undamaged sealing foil 22, the eddy currents IN induced in the electrically conductive layer of the sealing foil on account of the magnetic field generated by the transmission antenna 13 are distributed in a circular manner in the region of the pocket 21, as depicted in FIG. 9. An induction voltage $V_A$, $V_B$ arises in each case in the two reception coils 14, 15 on account of the respective flux linkage, said induction voltages being established by the measuring devices 166, 167 and forwarded to a control unit 160.

FIG. 7 shows the field and current distribution in the case of an unopened pocket 21 and undamaged foil 22 in the region of the pocket. In a sectional view, FIG. 7 shows the arrangement of the transmission coil 13 and the two reception coils 14, 15, which surround the hole 12 of the main body 10 of the apparatus 1. Depicted above the hole 12 is the foil 22 which seals the pocket 21. On account of the excitation in the transmission coil 13, an undisturbed magnetic field $B_T$ would arise in the region of the hole 12 if the foil 22 were absent. However, a counter-acting field $B_W$ arises due to the eddy currents $I_W$ induced in the foil 22, said counter-acting field in superposition with the excitation field $B_T$ producing a resultant field $B_{res}$, which is substantially attenuated in relation to the original excitation field $B_T$.

FIG. 8 shows a curve of the magnetic field generated by the transmission antenna 13, e.g. the magnetic field strength H or the magnetic flux density B over the coordinate direction x and the apparatus 1 and the blister pack 2 in a cross section. The curve of the field strength H is symmetrical in respect of the hole 12, i.e. the same magnetic field strength or flux density curve always prevails, irrespective of the position of the transmission antenna 13 from which the center of the hole 12 is approached. The induction voltage established at the reception antennas 14, 15 is in each case proportional to the integral under the respective flux density curve or the time derivative thereof. What emerges from FIG. 8 is that the flux linked with the two reception coils 14, 15, i.e. the integral of the flux density B, depicted in a hatched manner, over the area surrounded by the reception coils 14, is equal in the case of an undamaged foil 22 of the blister pack 2 and, accordingly, the difference $\Box V=(V_A-V_B)$ of the two induction voltages $V_A$, $V_B$ across the reception coils 14, 15 equals zero.

If the foil 22 sealing the pocket 21 rips, the eddy currents induced in the foil 22 under the pocket 21 are distributed irregularly.

Figure 10:
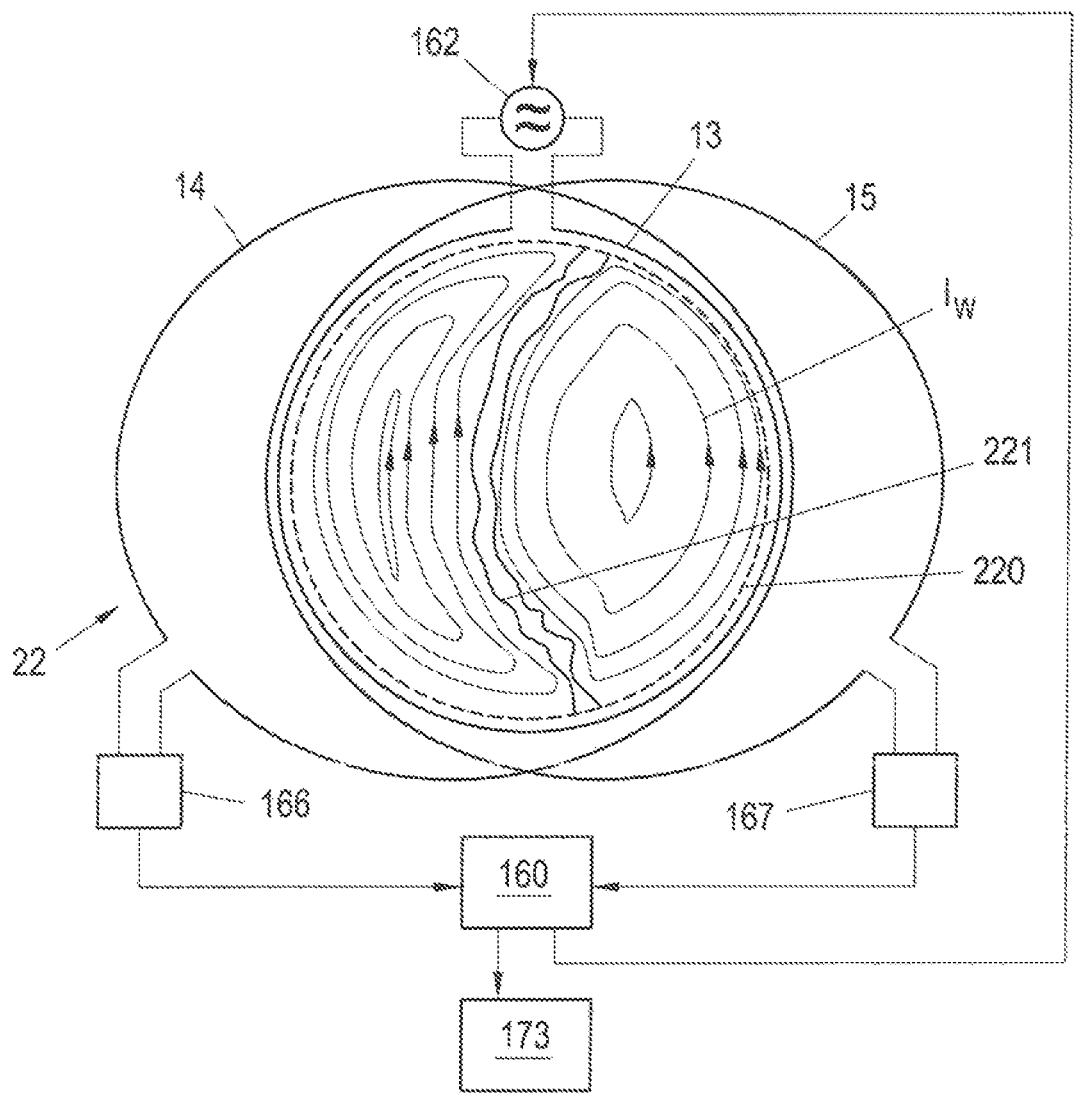
FIG. 10 shows, in detail, the field conditions in the region of an opened and ripped-open drug pocket and the actuation and the readout of the transmission and reception coils.

FIG. 10 depicts a current configuration of eddy currents $I_W$ when the foil 22 has ripped in the region of the pocket 21. Different voltages $V_A$, $V_B$ are induced in the two reception coils 14, 15 on account of the different alignment and size of the remains of the foil 22 which have arisen due to the rip, said different voltages being perceived via the voltage measuring devices 166, 167. In this case, the control unit 160 detects a voltage difference $\Box V$ and accordingly outputs a detection notification 173 indicating the detection of the ripping open or the removal of the medicament 23. Particularly large, and therefore easily detectable, voltage differences arise due to, in practice, the foil remains, which arise after the foil 22 was ripped open, at least slightly or partly turning out of the plane of the foil 22 underneath the pocket 21. As a result, the eddy currents induced in these foil remains also no longer flow in the plane of the foil 22, leading to a complex three-dimensional distribution of the resultant magnetic field $B_{res}$, which significantly deviates from the magnetic field distribution in the case of an undamaged sealing foil 22.

Figure 11:
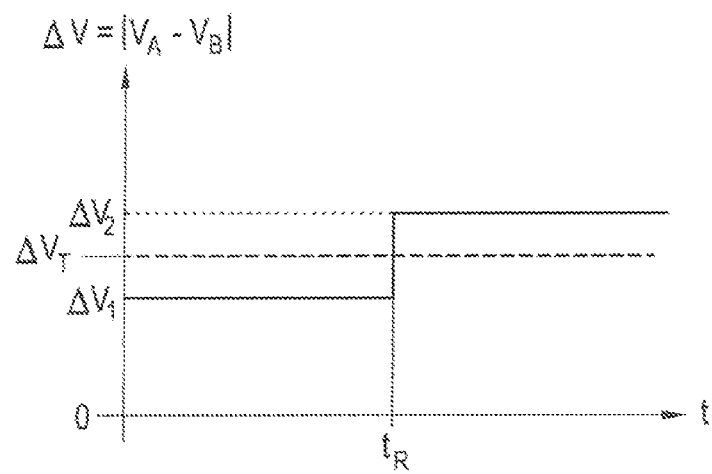
FIG. 11 shows a diagram of the voltage measurement values and the thresholds for the detection.

FIG. 11 shows a diagram in which the difference $\Box V=(V_A-V_B)$ of the voltage measurement values $V_A$, $V_B$ at the two reception coils 14, 15 is plotted against time, wherein the foil 22 of the blister pack 2 is ripped open in the region of the reception coils 14, 15 or of the hole 12 at a time $t_R$. The field conditions in the region of the reception coils 14, 15 change on account of the form of the rip, which never extends exactly symmetrically, and so a greater or smaller magnetic flux emanating from the transmission coil 13 is linked in each case with one of the reception coils 14, 15. These circumstances can be established by the detector unit 16 depicted in FIG. 12. In the present case, the magnitude of the difference of the voltages $V_A$, $V_B$ at the reception coils 14, 15 increases from a first voltage difference value $\Box V_1$, which is close to zero, to a voltage difference value $\Box V_2$, which exceeds a predetermined threshold $\Box V_T$. The presence of a rip in the foil 22 of the blister pack 2 can be deduced on account of this threshold $\Box V_T$ being exceeded.

Figure 12:
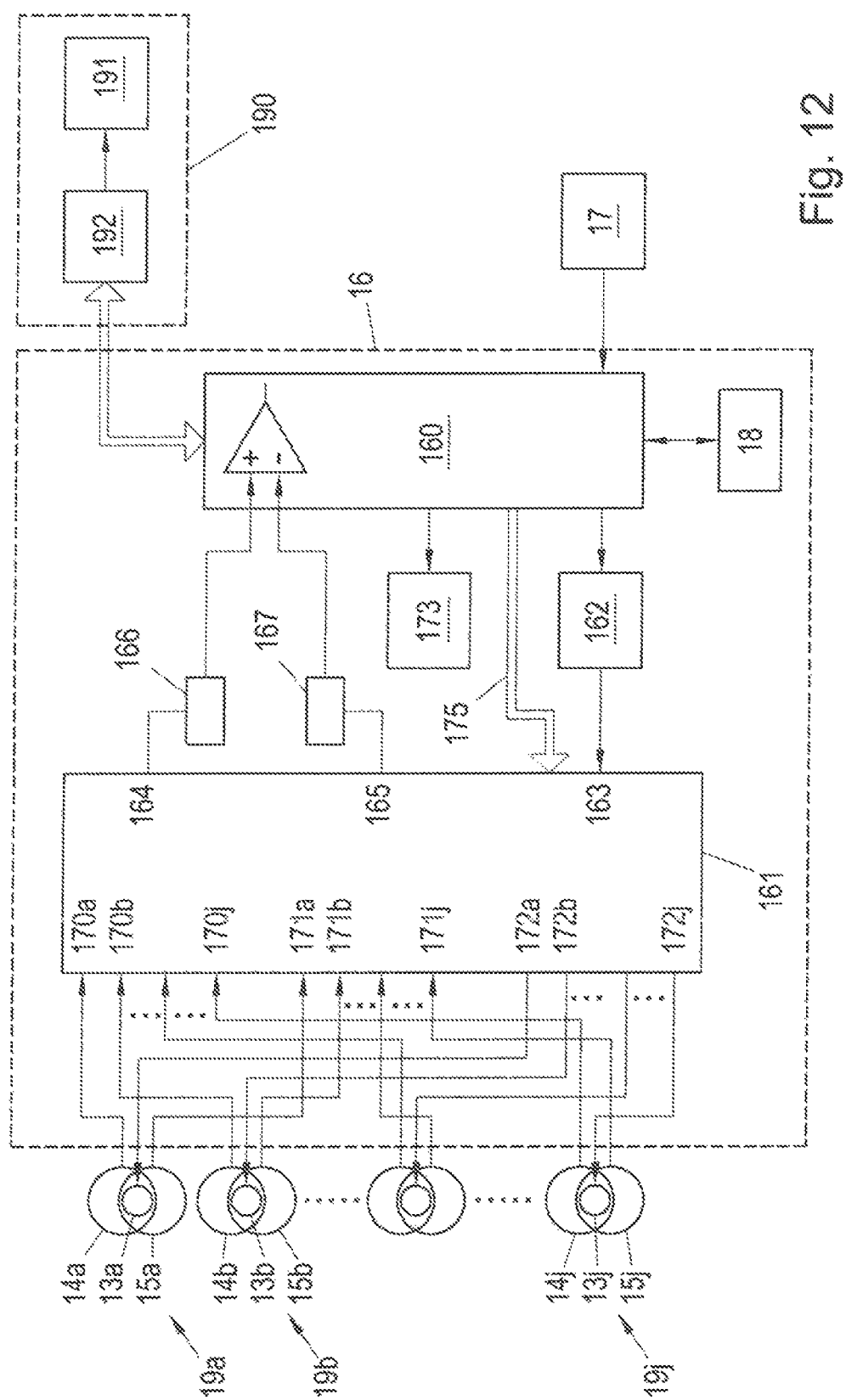
FIG. 12 schematically shows the electronic measurement or detection of the removal of medicaments.

FIG. 12 depicts a detector unit 16, by means of which the removal of a multiplicity of medicaments 23 can be detected from pockets in the same drug blister pack 2. Here, the detector unit 16 comprises the control unit 160 and a multiplexer 161 for selecting the respective group 19a . . . 19j, each comprising transmission and reception coils 13a . . . 13j, 14a . . . 14j and 15a . . . 15j assigned to one another. The multiplexer has a common input 163 for actuating the respective transmission antenna 13. The voltage generator 162, which is controlled by the control unit 160, is connected to this connector. Furthermore, the multiplexer 161 has two common outputs 164, 165, which are respectively assigned to one of the voltage measuring devices 166, 167. The results of the voltage measurement are transferred from the voltage measuring devices 166, 167 to the control unit 160. The control unit 160 furthermore sets by way of the multiplex control output 175 the respective group of transmission and reception coils 13a, 14a, 15a . . . 13j, 14j, 15j which are respectively addressed in order to establish whether the respective medicament 23 was removed from the respectively assigned pocket 21a . . . 21j. In a group-encompassing manner, the multiplexer 161 in each case has two multiplex inputs 170a, 171a . . . 170j, 171j and one multiplex output 172a . . . 172j, wherein each one of the groups is separately addressable in each case. The multiplex inputs and multiplex outputs, which are assigned to one another in groups 19a . . . 19j, are each connected to transmission and reception antennas 13a . . . 13j, 14a . . . 14j, 15a . . . 15j, which are assigned to one another and grouped and arranged in the region of the same hole 12.

In order to detect whether the metallic foil 22 resting against the main body 10 in the region of the respective hole 12 is undamaged, in particular free from rips, the difference of the voltage induced in the reception coils 14, 15 as a result of an electric current in the transmission coil 13 is measured. If it lies below a predetermined threshold, the foil 22 can be considered to be undamaged in the region of the respective hole 12.

The detector unit 16 measures the two voltages across the reception coils 14, 15 and determines the difference between the voltages across the reception coils 14, 15. In the case where the difference in the two voltages exceeds a predetermined threshold, said detector unit outputs a notification which indicates the presence of a rip in the metal foil 22 sealing the respective pocket 21.

In order to enable communication with an external data communications device, the control unit 160 is connected to a short-range radio module 190 comprising an antenna 191 and a communication controller 192. This short-range radio module can be an RFID or NFC transponder, as well as use an alternative wireless short-range communications technology, such as e.g. Bluetooth. Furthermore, the control unit 160 is connected to a storage 18, wherein the control unit 160, if the removal of a medicament 23 from one of the pockets is detected, in each case stores a message in this respect in the storage 18 and keeps it available for retrieval on the part of an external data communications device.

In particular, the detector unit 16 and the short-range radio module 190 can also be housed in a separate housing and the detector unit 16 is electrically connected to the transmission antennas 13 and reception antennas 14, 15 arranged on or in the main body 10 by way of non-destructively separable electric contacts.

Furthermore, FIG. 12 depicts a recording unit 17, which triggers the recording of the removal of medicaments at predetermined time intervals. The recorded values or messages which represent the removal of medicaments are stored in the storage 18.

Figure 13:
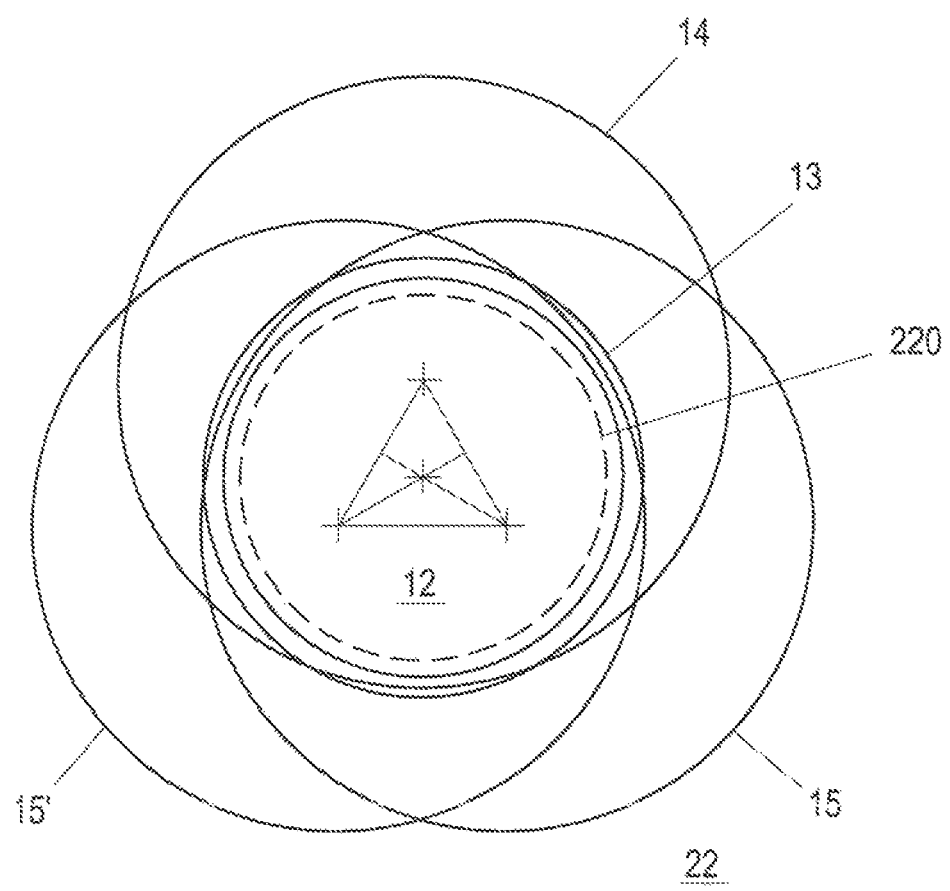

FIG. 13 depicts an alternative embodiment of the arrangement of transmission and reception coils. This special arrangement comprises a transmission coil 13 and three reception coils 14, 15, 15', which all have a circular embodiment. The centers of the reception coils 14, 15, 15' are situated on an equilateral triangle, the center of the transmission coil 13 lying at the centroid thereof. Furthermore, the edge 220 of the pocket 21 which is adjoined by the foil 22 has a concentric embodiment in respect of the transmission coil 13.

Figures 14, 15:
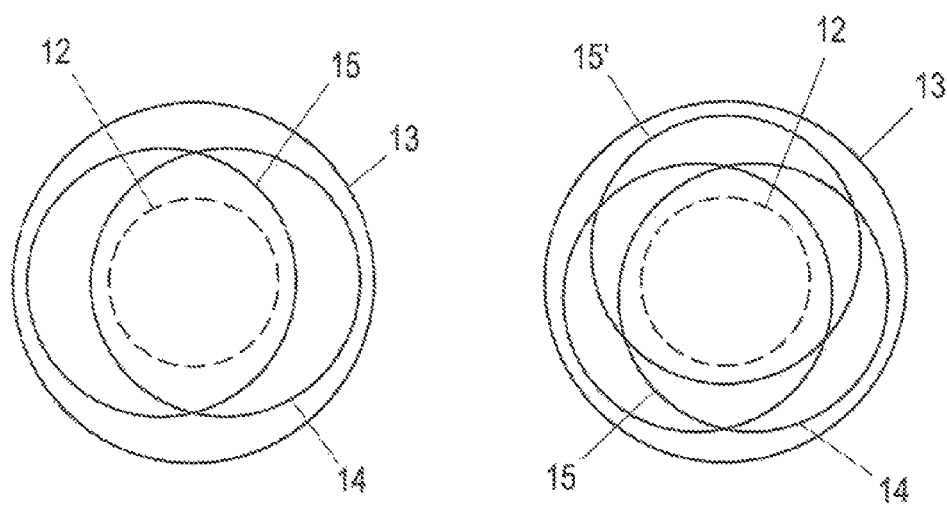
FIGS. 13 to 15 show alternative coil arrangements with one transmission coil and two or three reception coils.

FIGS. 14 and 15 show further alternative coil arrangements with one transmission coil 13 and two or three reception coils 14, 15, 15', wherein the transmission coil in this case completely surrounds the reception coils.

Figure 16:
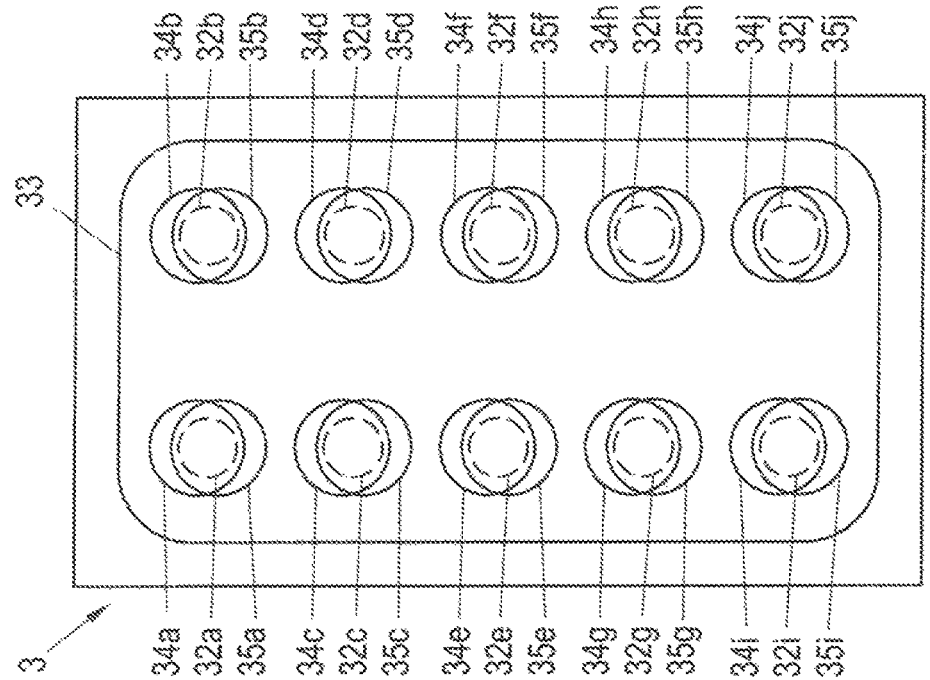

FIG. 16 shows a further apparatus 3 in accordance with a second embodiment of the invention in more detail. Like the apparatus 1 presented above, this apparatus 3 also has a number of holes 32a-32j which are surrounded by a transmission coil 33 and reception coils 34a . . . 34j, 35a . . . 35j. However, in contrast to the apparatus 1 in accordance with the first embodiment of the invention, the apparatus 3 does not have one transmission coil 33a . . . 33j per hole 32a . . . 32j, but only a single transmission coil 33 for all holes 32a . . . 32j. The transmission coil 33 depicted in FIG. 16 surrounds and encloses all reception coils 34a . . . 34j, 35a . . . 35j, the arrangement of which corresponds to the arrangement of the reception coils 34a . . . 34j, 35a . . . 35j of the apparatus 1 in accordance with the first embodiment of the invention, i.e. two reception coils 34a, 35a, . . . , 34j, 35j assigned to one another are each arranged in the region of in each case one of the holes 32a . . . 32j.

Figure 17:
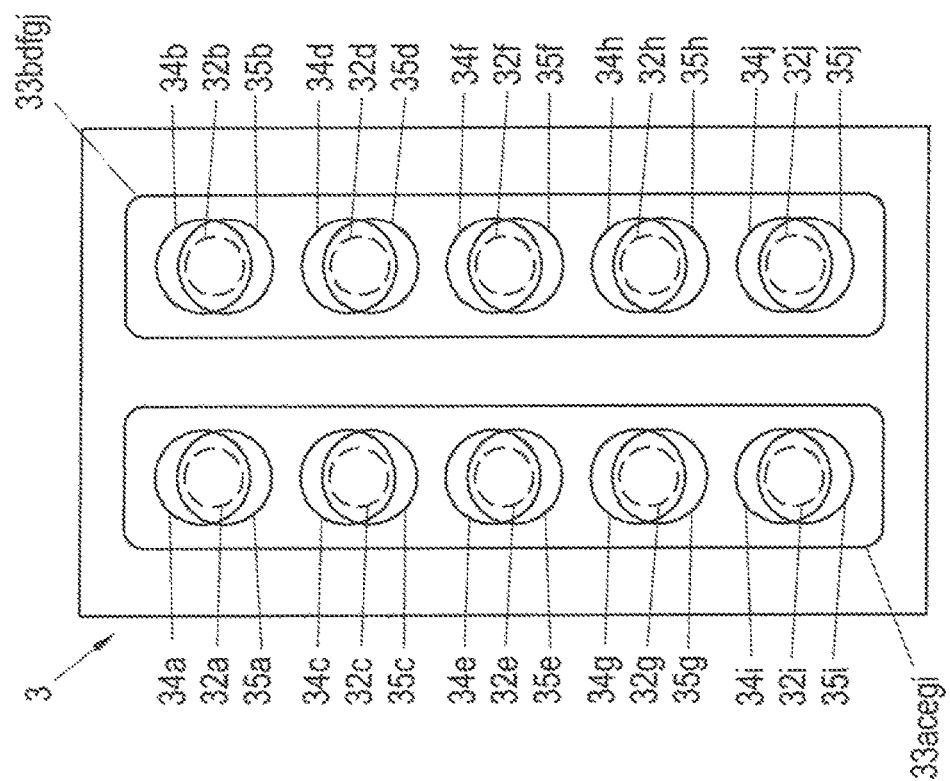

FIGS. 17 to 19 show minor modifications of the further apparatus 3, which respectively comprise a plurality of transmission coils 33 instead of a single transmission coil 33, with each transmission coil respectively surrounding a subset of the reception coils 34a . . . 34j, 35a . . . 35j, wherein all transmission coils 33 overall in each case surround all reception coils 34a . . . 34j, 35a . . . 35j and each pair of reception coils 34a . . . 34j, 35a . . . 35j assigned to one another is surrounded in each case by exactly one transmission coil 33.

FIG. 20 shows an illustration analogous to FIG. 8, wherein a curve is depicted which shows the magnetic field generated by the transmission antenna 33, e.g. in the form of the magnetic field strength H or the magnetic flux density B in the region of a hole 32. However, the curve of the field strength H or the flux density B is not symmetrical in relation to the hole 32. The induction voltage $V_A$, $V_B$ established at the reception antennas 34, 35 is in each case proportional to the integral under the respective flux density curve or the time derivative thereof. What emerges from FIG. 20 is that the flux linked to the two reception coils 34, 35, i.e. the integral of the flux density over the surrounded area, is not the same for both reception coils 34, 35 in the case of an undamaged foil 22 of the blister pack 2 and the difference of the two voltages $V_A$-$V_B$ across the reception coils 34, 35 accordingly does not equal zero.

If the foil 22 sealing the pocket 21 rips, the eddy currents induced in the foil 22 under the pocket 21 have a different distribution and the established voltage difference $V_A$-$V_B$ changes.

Figure 21:
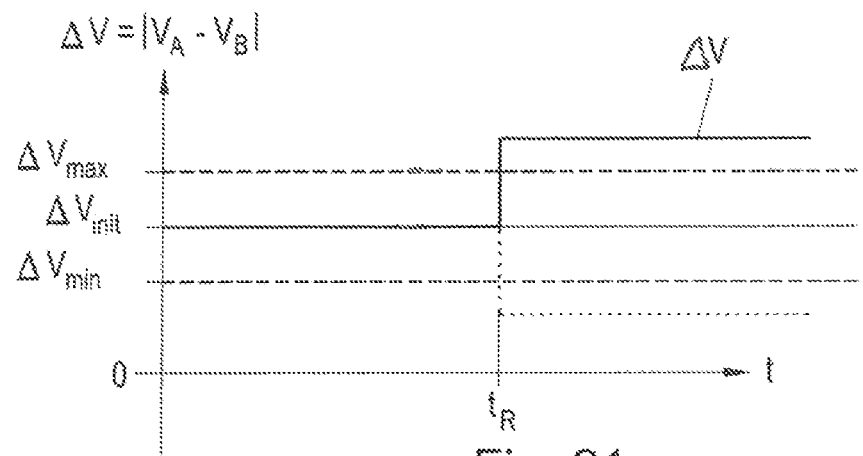
FIG. 21 shows a diagram of the voltage measurement values and the thresholds for the detection.

FIG. 21 shows a diagram in which the difference $\Box V$ of the voltage measurement values $V_A$, $V_B$ across the two reception coils 34, 35 is plotted over time, wherein the foil 22 of the blister pack 2 is ripped open in the region of the reception coils 34, 35 or of the hole 32 at a time tR. A voltage difference $\Box V$ which differs from zero already emerges in the case of an intact foil 22 as a result of the asymmetric arrangement, depicted in FIG. 20, of the two reception coils 34, 35 in relation to the transmission coil. This voltage difference $\Box V$ in the case of an intact foil is buffer stored as reference voltage difference $V_{init}$ and kept available for further comparisons.

If a rip is created in the foil 22 at the time $t_R$, there is also a change in the field conditions in the region of the reception coils 34, 35 such that a greater or smaller magnetic flux emanating from the transmission coil 33 is linked with one of the reception coils 34, 35 in each case. These circumstances can be established by the detector unit 360 shown in FIG. 22. In this case, the magnitude of the difference $\Box V$ of the voltages $V_A$, $V_B$ across the reception coils 34, 35 from the reference voltage difference $\Box V_{init}$ increases or decreases to a greater or smaller voltage difference value. In order to detect such deviations, the established voltage difference values are compared to two thresholds $\Box V_{min}$ and $\Box V_{max}$. If the respective voltage difference value $\Box V$ is situated within the interval defined by the two thresholds $\Box V_{min}$, $\Box V_{max}$, the foil 22 of the blister pack 2 is considered to be intact; otherwise the foil 22 is considered to be ripped and a corresponding message is output.

Figure 22:
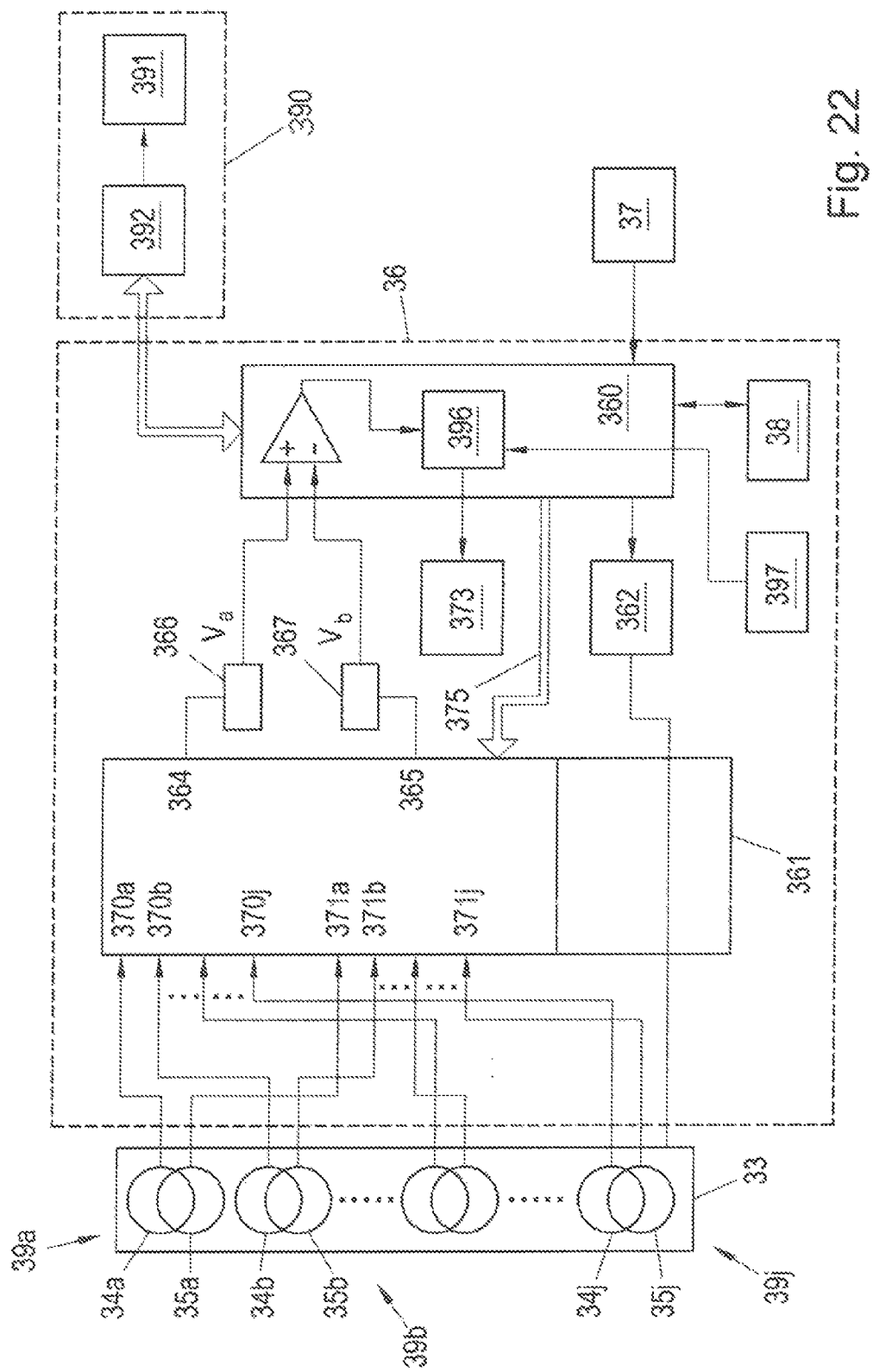
FIG. 22 schematically shows the electronic measurement in the case of one of the embodiments of the invention depicted in FIGS. 16 to 21.

FIG. 22 shows the electronic measurement or electronic determination of a rip by means of an apparatus 3 in accordance with the second embodiment of the invention, wherein the presented measurement substantially corresponds to the measuring apparatus depicted in FIG. 12. FIG. 22 depicts a detector unit 36, by means of which the removal of a multiplicity of medicaments 23 from pockets 21 of the same drug blister pack 2 can be detected. Here, the detector unit 36 comprises the control unit 360, which controls the progress of the measurement. The transmission coil 33 is connected directly to the voltage generator 362, which is controlled by the control unit 360.

The detector unit 36 furthermore comprises a multiplexer 361 for selecting the respective group 39a . . . 39j, respectively comprising reception coils 34a . . . 34j and 35a . . . 35j assigned to one another. The multiplexer 361 has two common outputs 364, 365, which are respectively assigned to one of the voltage measurement units 366, 367. The results $V_A$, $V_B$ of the voltage measurement are transferred from the voltage measuring devices 366, 367 to the control unit 360.

The control unit 360 furthermore sets by way of the multiplex control output 375 the respective group of reception coils 34a . . . 34j, 35a . . . 35j, which are respectively addressed in order to establish whether the respective medicament 23 was removed from the respectively assigned pocket 21a . . . 21j. In a group-encompassing manner, the multiplexer 361 in each case has two multiplex inputs 370a, 371a . . . 370j, 371j, wherein each one of the groups 19a . . . 19j is separately addressable in each case. The multiplex inputs, which are assigned to one another in groups 19a . . . 19j, are each connected to reception coils 14a . . . 14j, 15a . . . 15j, which are assigned to one another and grouped and arranged in the region of the same hole 12.

In order to improve the detection accuracy, it is possible, prior to the actual detection of rips with each one of the individual reception coils 34a . . . 34j, 35a . . . 35j, to establish the size of the respectively induced voltage $V_A$, $V_B$ in the case of an undamaged or original blister pack 2 with an intact foil 22 if a predetermined AC voltage is applied across the transmission coil 33. The voltage values $V_A$, $V_B$ established by the individual reception coils 34a . . . 34j, 35a . . . 35j or the difference $\Box V_{init}$ of the voltages of in each case two reception coils 34a, 35a, . . . , 34j, 35j assigned to one another are stored in a reference value storage 397 in this case and kept available for a subsequent comparison.

In order to detect whether the metallic foil 22 resting against the main body 30 in the region of the respective hole 32 is undamaged, in particular free from rips, the difference $\Box V$ of the voltages applied in the reception coils 34, 35 is measured. Subsequently, a comparison unit 396 is used to compare the measured difference $\Box V$ with the reference voltage difference $\Box V_{init}$ stored in the reference value storage 397 for the respective reception coils. Alternatively, the comparison unit 396 can also compare the measured difference $\Box V$ with the difference $\Box V_{init}$ of the reference voltage measurement values established for the respective reception coils in the reference value storage 397. If the voltage difference $\Box V$ differs from the reference voltage difference $\Box V_{init}$ by a predetermined threshold, a rip counts as detected. To this end, as depicted in FIG. 22, the established voltage difference $\Box V$ and the reference voltage difference $\Box V_{init}$ are respectively compared to one another by the comparison unit 396. If the voltage difference $\Box V$ lies within an interval around the reference voltage difference $\Delta V_{init}$ with the upper limit $V_{max}$ and the lower limit $V_{min}$, the foil 22 in the region of the respective hole 32 is considered to be undamaged; otherwise, it is considered to be ripped.

In order to enable communication with an external data communications device, the control unit 360 is connected to a short-range radio module 390, which comprises an antenna 391 and a communication controller 392. This short-range radio module can be an RFID or NFC transponder, as well as use an alternative wireless short-range communications technology, such as e.g. Bluetooth. Furthermore, the control unit 360 is connected to a storage 38, wherein the control unit 360, if the removal of a medicament 23 from one of the pockets is detected, in each case stores a message in this respect in the storage 38 and keeps it available for retrieval on the part of an external data communications device.

In particular, the detector unit 36 and the short-range radio module 390 can also be housed in a separate housing and the detector unit 36 is electrically connected to the transmission antennas 33 and reception antennas 34, 35 arranged on or in the main body 30 by way of non-destructively separable electric contacts.

Furthermore, FIG. 22 depicts a recording unit 37, which triggers the recording of the removal of medicaments at predetermined time intervals. The recorded values or messages which represent the removal of medicaments are stored in the storage 38.

Figure 23:
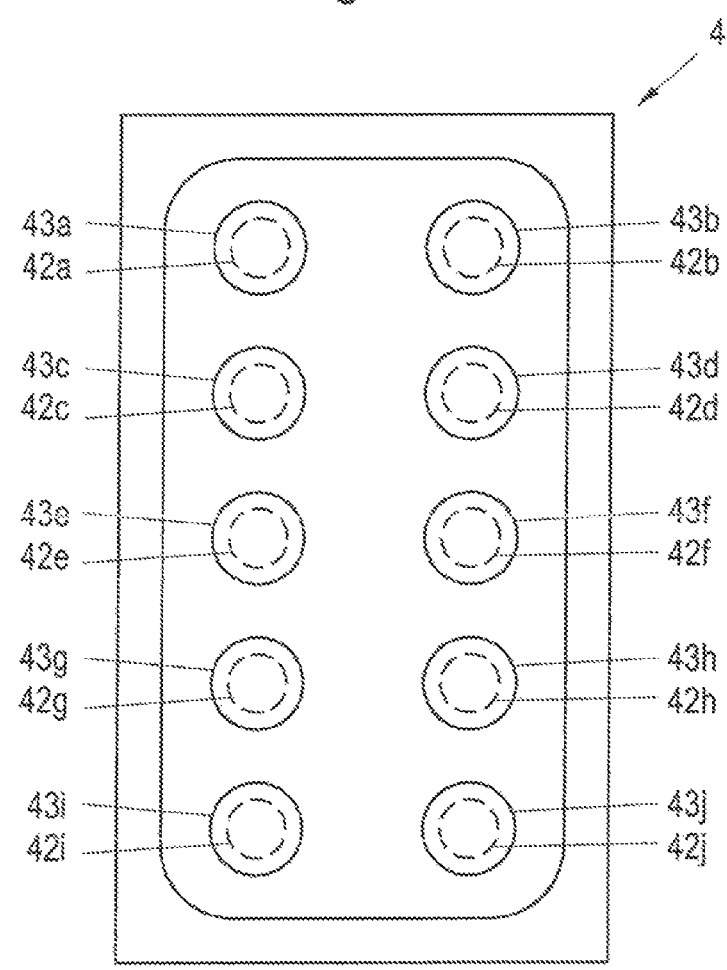
FIG. 23 shows a further embodiment of the invention with a single coil per hole.

FIG. 23 shows a further apparatus 4 in accordance with a third embodiment of the invention with a single coil 43a . . . 43j per hole 42a . . . 42j. The respective coil 43 serves both as transmission coil and as reception coil. By determining the respective inductance or impedance of the coil 43, which, in addition to the coil geometry, also depends substantially on the media situated in the region of the coil 43, it is possible to establish whether the foil 22 of the blister pack 2 is ripped in the region of the coil 43.

Figure 24:
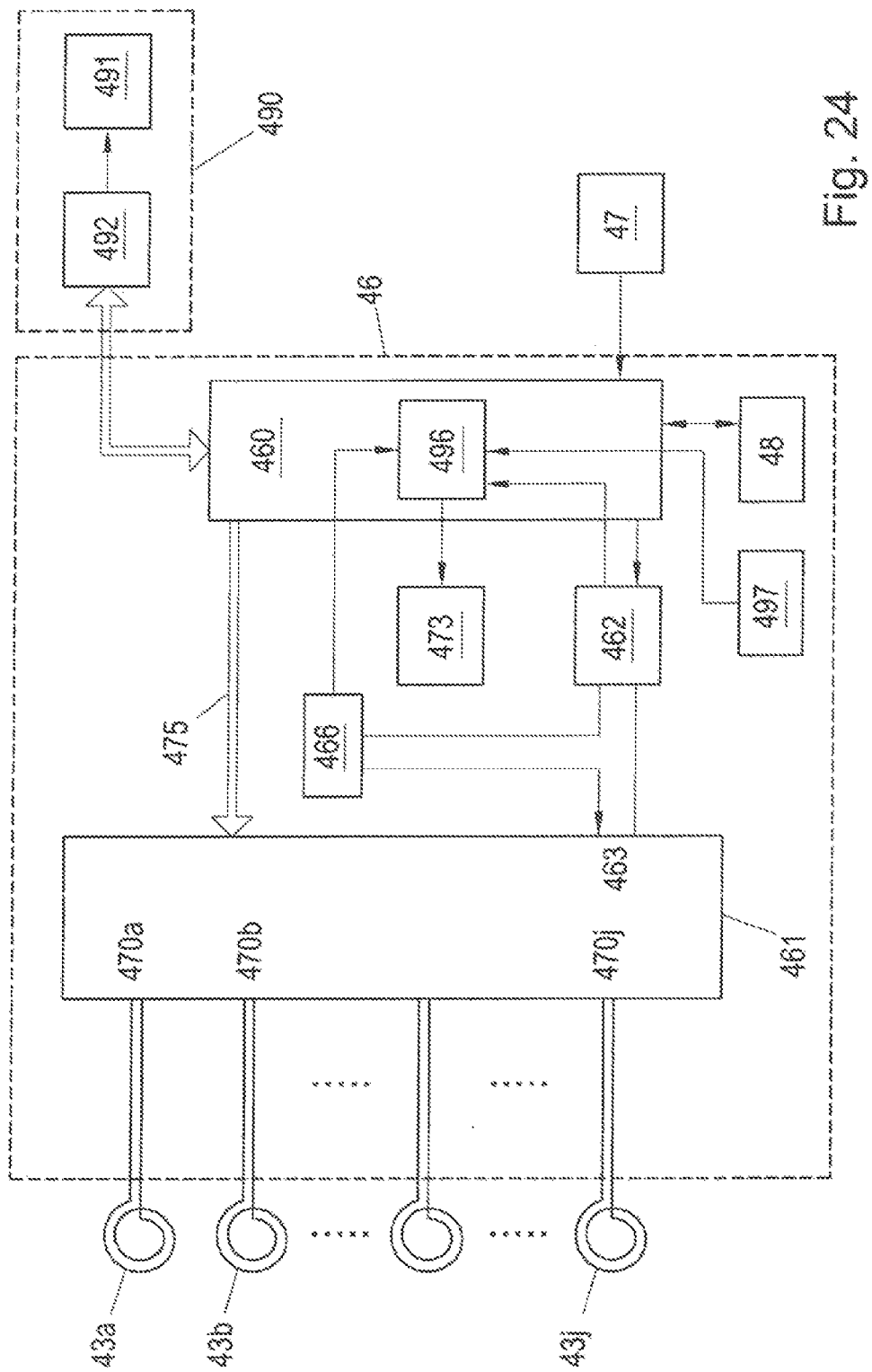
FIG. 24 schematically shows the electronic measurement in the case of an embodiment of the invention depicted in FIG. 23.

FIG. 24 schematically shows the electronic measurement in the case of an apparatus 4 depicted in FIG. 23. The depicted apparatus 4 substantially corresponds to the measurement apparatus depicted in FIG. 12. It is possible to detect the removal of a multiplicity of medicaments 23 from pockets 21 of the same drug blister pack 2 using the detector unit 46. In this case, the detector unit 46 comprises the control unit 460, which controls the progress of the measurement.

The detector unit 46 furthermore comprises a multiplexer 461 for selecting the respective coil 43a . . . 43j. The multiplexer 461 has a common bipolar output 463, which is connected to the voltage generator 462. A current measuring device 466 is arranged in one of the connection lines between the voltage generator 462 and the common input 463 of the multiplexer 461. Both the voltage 462 across the voltage generator 462 and the current established by the current measuring device 466 are fed to the control unit 460.

The control unit 460 furthermore by way of the multiplex control output 475 sets the respective coil 43a . . . 43j which is addressed in each case to establish whether the respective medicament 23 was removed from the respectively assigned pocket 21a . . . 21j. The multiplexer 461 has respectively bipolar multiplex connectors 470a . . . 470j, wherein each coil 43a . . . 43j is separately addressable in each case.

In order to improve the detection accuracy, it is possible, prior to the actual detection of rips with each one of the individual coils 43a . . . 43j, to establish the magnitude of the respective impedance of the coil 43a . . . 43j in the case of an undamaged or original blister pack 2 with an intact foil 22. The voltages applied across the individual coils 43a . . . 43j and the currents respectively established by the current measuring device 466 are related to one another and the established impedance, e.g. with the real and imaginary part thereof or with the magnitude and phase thereof, is stored in a reference value storage 497 as a reference impedance for a subsequent comparison.

In order to detect whether the metallic foil 22 resting against the main body in the region of the respective hole 32 is undamaged, in particular free from rips, the impedance of the respective coil 43a . . . 43j is determined and the impedance established thus is compared by a comparison unit 496 with the reference impedance stored in the reference value storage 497. The respective deviation of the real part and of the imaginary part or of the phase and magnitude is established and compared to a threshold value. If the deviation exceeds the threshold value, the assumption is made that the metallic foil 22 of the blister pack 2 is ripped and a corresponding message 473 is output.

In order to enable communication with an external data communications device, the control unit 460 is connected to a short-range radio module 490 comprising an antenna 491 and a communication controller 492. This short-range radio module can be an RFID or NFC transponder, as well as use an alternative wireless short-range communications technology, such as e.g. Bluetooth. Furthermore, the control unit 460 is connected to a storage 38, wherein the control unit 460, if the removal of a medicament 23 from one of the pockets is detected, in each case stores a message in this respect in the storage 38 and keeps it available for retrieval on the part of an external data communications device.

In particular, the detector unit 46 and the short-range radio module 490 can also be housed in a separate housing and the detector unit 46 is connected to the antennas 43*a* . . . 43*j* arranged on or in the main body by way of non-destructively separable electric contacts.

Furthermore, FIG. 24 depicts a recording unit 47, which triggers the recording of the removal of medicaments at predetermined time intervals. The recorded values or messages which represent the removal of medicaments are stored in the storage 48.

One or more measurement frequencies in the frequency range between 100 Hz and 100 MHz are used in all embodiments for actuating the coil.

The invention claimed is:

1. An apparatus for detecting a removal of medicaments from a drug blister pack, comprising:
   a main body for accommodating the drug blister pack and having a base area embodied to rest against an electrically conductive metallic foil of the drug blister pack which seals off pockets of the drug blister pack, said main body having holes formed therein in a region of the pockets of the drug blister pack, said holes being embodied for a passage of the medicaments situated in the pockets of the drug blister pack, each of said holes is disposed in the region of one of the pockets in each case;
   at least one coil disposed in a region of each of said holes, said coil surrounding a respective one of said holes; and
   a detector unit for generating at least one of an electric field or a magnetic field in the region of at least one of said holes by means of said coil and evaluates a voltage across or a current applied to said coil surrounding said respective hole.

2. The apparatus according to claim 1, wherein said coil includes a transmission coil surrounding said respective hole, and at least one reception coil disposed a region of said respective hole in each case, said reception coil surrounding said respective hole.

3. The apparatus according to claim 2, wherein said reception coil is one of at least two reception coils disposed in said region of said respective hole in each case, said reception coils surrounding said respective hole.

4. The apparatus according to claim 2, wherein said transmission coil is a separate transmission coil in each case for each of said holes.

5. The apparatus according to claim 3, wherein said reception coils are assigned to one another in respect of said transmission coil and disposed in such a way that, in a case where the electrically conductive metallic foil resting on said main body in said region of said respective hole is undamaged, a difference of voltages induced in said reception coils as a result of an electric current in said transmission coil lies below a predetermined threshold.

6. The apparatus according to claim 5, wherein said detector unit activates said transmission coil and measures the voltages across said reception coils and establishes a difference between the voltages across said reception coils and, in a case where the difference of the two voltages exceeds the predetermined threshold, emits a message which indicates a presence of a rip in a region of said reception coils in the electrically conductive metallic foil sealing a respective pocket.

7. The apparatus according to claim 3, wherein said detector unit further comprises:
   a control unit activating said transmission coil;
   a measuring unit for measuring voltages across said reception coils;
   a reference value memory for storing all measured voltages at an initial time, after a new, undamaged drug blister pack was placed into the apparatus; and
   a comparison unit for determining a removal of the medicaments from the drug blister pack, said comparison unit establishing a difference in each case between a voltage stored by said reference value memory and a voltage currently established by said measuring unit and said comparison unit outputting a message in a case where the difference exceeds a predetermined threshold which indicates a presence of a rip in the electrically conductive metallic foil sealing the respective pocket in a region of said reception coils.

8. The apparatus according to claim 3, wherein said detector unit further comprises:
   a control unit activating said transmission coil;
   a measuring unit for measuring voltages across said reception coils and establishes a voltage difference of measured voltages;
   a reference value memory for storing all established voltage differences at an initial time, after a new, undamaged drug blister pack was placed into the apparatus; and
   a comparison unit for determining a removal of the medicaments from the drug blister pack, said comparison unit establishing a difference in each case between the voltage difference stored by said reference value memory and the voltage difference currently established by said measuring unit and said comparison unit outputting a message in a case where the difference exceeds a predetermined threshold which indicates a presence of a rip in the electrically conductive metallic foil sealing the respective pocket in said region of said reception coils.

9. The apparatus according to claim 1, wherein:
   said coil includes in each case exactly one separate coil surrounding each of said holes;
   said detector unit applies an electric voltage across said separate coil and measures an electric current flowing through said separate coil and, from this, establishes at least one of an impedance of said separate coil, a resistance of said separate coil and a reactance of said separate coil, and said detector unit identifies an exceeding of a predetermined impedance threshold and/or predetermined thresholds for the resistance and the reactance of said separate coil and in this case outputs a message which indicates a presence of a rip in the electrically conductive metallic foil sealing the respective pocket in a region of said separate coil.

10. The apparatus according to claim 1, further comprising:
    a memory; and
    a recording unit, which activates said detector unit at predetermined intervals and establishes a presence of rips in the electrically conductive metallic foils sealing off the pockets of the drug blister pack and stores information in this respect in said memory and keeps it available for further queries.

11. The apparatus according to claim 1, further comprising:
    a short-range radio module having an antenna and a communication controller, said short-range radio module being connected to said detector unit; and a memory which, if a rip in the electrically conductive metallic foil is identified, stores a message in this respect, with an additional provision of a timestamp, wherein said detector unit transfers information stored in said memory to an external data communications device.

12. The apparatus according to claim 11, wherein said short-range radio module is a radio-frequency identification or near field communication transponder having said transponder antenna and said communication controller.

13. The apparatus according to claim 12, wherein said transponder antenna extends at least in part along an outer boundary of said main body.

14. The apparatus according to claim 12, wherein said short-range radio module having said antenna and said communication controller, operates on a basis of a Bluetooth standard.

15. The apparatus according to claim 3,
further comprising an excitation unit connected to said transmission coil;
further comprising two measuring units connected to said reception coils; and
wherein said detector unit has a control unit for actuating said excitation unit to excite said transmission coil and actuates said measuring units to measure induction voltages across said reception coils, said detector unit establishes a difference of established induction voltages and outputs a signal in a case where a magnitude of a difference exceeds a predetermined threshold.

16. The apparatus according to claim 15,
further comprising a multiplexer for selecting a group in each case containing said transmission coil and said reception coils assigned to one another, said multiplexer is connected to said detector unit, said multiplexer has a common input for actuating said transmission coil and two common outputs for obtaining induction voltages obtained from said reception coils, said common input is connected to said excitation unit and said common outputs are each connected to one of said measuring units; and
wherein said multiplexer has groups, each containing two multiplex inputs and one multiplex output, which are addressable together and are each connected to said transmission coil and said reception coils, which are assigned to one another and disposed in a region of a same one of said holes.

17. The apparatus according to claim 3, wherein said reception coils are disposed in a symmetric manner in respect of said holes and in respect of said transmission coil.

18. The apparatus according to claim 11, further comprising a housing, at least one of said detector unit or said short-range radio module is housed in said housing, and said detector unit is electrically connected by way of electric contacts, which are separable in a non-destructive manner, to said transmission coil and said reception coils disposed at or in said main body.

19. A configuration, comprising:
a drug blister pack having a number of pockets containing medicaments and an electrically conductive metallic foil sealing off said pockets;
an apparatus for detecting a removal of said medicaments from said drug blister pack, said apparatus containing:
a main body accommodating said drug blister pack and having a base area embodied to rest against said electrically conductive metallic foil of said drug blister pack, said main body having holes formed therein in a region of said pockets of said drug blister pack, said holes being embodied for a passage of said medicaments situated in said pockets of said drug blister pack, each of said holes is disposed in a region of one of said pockets in each case;
coils disposed in the region of each of said holes, said coils surrounding a respective one of said holes, said coils including a transmission coil and at least two reception coils in each case lying opposite each of said holes; and
a detector unit for generating at least one of an electric field or a magnetic field in a region of at least one of said holes by means of said coils and evaluates a voltage across or a current applied to said coils surrounding said respective hole.

* * * * *